US009404821B2

(12) United States Patent
He et al.

(10) Patent No.: US 9,404,821 B2
(45) Date of Patent: Aug. 2, 2016

(54) LARGE DEFORMATION TENSILE TESTING SYSTEM

(75) Inventors: Manchao He, Beijing (CN); Xiaojie Yang, Beijing (CN); Yi Zhang, Beijing (CN)

(73) Assignee: China University of Mining & Technology (Beijing), Beijing (CN)

( * ) Notice: Subject to any disclaimer, the term of this patent is extended or adjusted under 35 U.S.C. 154(b) by 18 days.

(21) Appl. No.: 14/388,959

(22) PCT Filed: Mar. 31, 2012

(86) PCT No.: PCT/CN2012/073423
§ 371 (c)(1),
(2), (4) Date: Sep. 29, 2014

(87) PCT Pub. No.: WO2013/143149
PCT Pub. Date: Oct. 3, 2013

(65) Prior Publication Data
US 2015/0059489 A1  Mar. 5, 2015

(51) Int. Cl.
*G01N 3/08* (2006.01)
*G01L 5/08* (2006.01)
(Continued)

(52) U.S. Cl.
CPC .............. *G01L 5/08* (2013.01); *G01M 5/0058* (2013.01); *G01N 3/08* (2013.01); *G01N 3/10* (2013.01); *G01N 2203/028* (2013.01)

(58) Field of Classification Search
CPC ......... G01L 5/08; G01M 5/0058; G01N 3/08; G01N 3/10; G01N 2203/028
USPC .................................................. 73/760, 828
See application file for complete search history.

(56) References Cited

U.S. PATENT DOCUMENTS 3,010,311 A   11/1961   Meldrum et al.
4,475,404 A   10/1984   Rutledge, Jr. et al.
(Continued)

FOREIGN PATENT DOCUMENTS

CN    2567557 Y    8/2003
CN    101013056 A  8/2007
(Continued)

OTHER PUBLICATIONS

International Search Report of Application No. PCT/CN2012/073423, mailed Aug. 16, 2012.
(Continued)

*Primary Examiner* — Max Noori
(74) *Attorney, Agent, or Firm* — Yunling Ren; Eaton & Van Winkle (57) ABSTRACT

A large deformation tensile testing system, for use in testing a large deformation tensile of an anchor rod or an anchor rode, comprising a main machine frame (1), a rear collet component (2) arranged at a first position on the longitudinal direction of the main machine frame (1), a front collet component (3) movably arranged at a second position on the longitudinal direction of the main machine frame (1), a telescoping apparatus (4), a measurement and control apparatus, where a sensor module thereof senses the displacement and real-time tensile of the telescoping apparatus to form real-time data to be transmitted to an analysis module and a control module, the control module that controls, on the basis of a set measurement and control scheme and of an input of the sensor module, a testing process to proceed according to a set testing condition, the analysis module for analyzing the input of the sensor module to form a test result, and an output module for outputting same. The large deformation tensile testing system is capable of deriving a statics parameter of the anchor rod or anchor rode being tested.

8 Claims, 5 Drawing Sheets

(51) Int. Cl.
　　*G01N 3/10*　　　　(2006.01)
　　*G01M 5/00*　　　　(2006.01)

(56) References Cited

U.S. PATENT DOCUMENTS

| | | | |
|---|---|---|---|
| 4,607,586 A * | 8/1986 | Taquino | E02B 17/003 |
| | | | 114/219 |
| 4,615,221 A * | 10/1986 | Mellor | G01N 3/10 |
| | | | 73/778 |
| 4,939,939 A | 7/1990 | Vemmer | |
| 5,911,166 A * | 6/1999 | Cowan | G01N 3/08 |
| | | | 73/831 |
| 6,142,023 A | 11/2000 | Cole et al. | |
| 2002/0164220 A1* | 11/2002 | Sailing | B23B 31/006 |
| | | | 409/131 |
| 2007/0022675 A1* | 2/2007 | Weisman | G01L 5/042 |
| | | | 52/146 |

FOREIGN PATENT DOCUMENTS

| | | |
|---|---|---|
| CN | 100533084 C | 8/2009 |
| CN | 201532275 U | 7/2010 |
| CN | 101858225 A | 10/2010 |
| JP | 59061748 | 4/1984 |
| JP | 6319533 | 1/1988 |
| JP | 2222824 | 9/1990 |
| JP | 5-322726 A | 12/1993 |
| JP | 2001021469 A | 1/2001 |
| JP | 2003106964 A | 4/2003 |
| JP | 2005337819 A | 12/2005 |
| KR | 10-0856734 B1 | 9/2008 |

OTHER PUBLICATIONS

EESR issued Oct. 2, 2015 by the EP Office.
Office Action issued Sep. 15, 2015 by the JP Office.

* cited by examiner

LARGE DEFORMATION TENSILE TESTING SYSTEM

CROSS-REFERENCE TO RELATED PATENT APPLICATIONS

This is a national stage application of PCT/CN2012/073423, filed on Mar. 31, 2012 under 35 U.S.C. 371, which is incorporated reference in its entirety.

TECHNICAL FIELD

The present disclosure relates to a large deformation tensile testing machine, and in particular to a large deformation tensile testing system for an indoor research of statics performances of anchor bolts (ropes) having constant-resistance and large deformation and other common anchor shanks (ropes).

BACKGROUND

In recent years, as the rapid development of the national economy, there is increasing demand for energy in various industries. Open-cut mines in China have now in the stage of deep mining one after the other. The problems such as a large quantity of slopes, active faults and the stability of surrounding rocks in chambers are involved in the fields of mining, water conservancy, transportation and the like.

At present, China is in a period of rapid development of various engineering constructions. In the process of mineral exploitation and underground engineering construction, there have been many disasters: rock outburst, pressure bump, collapse and the like. For control of natural disasters and engineering disasters in the case of high and steep slopes and stable surrounding rocks of roadways, it mainly relies on a traditional prestressed anchor bolt (rope) reinforcement system and derivative supporting structure engineering thereof. However, since the instability of rock mass reinforcing structures is mostly caused by large deformation due to elastic-plasticity, the supporting and reinforcing concept based on the traditional prestressed anchor shank (rope) system has been unable to adapt to the large deformation development law of rock masses (slope rock masses and tunnel surrounding rocks), and hence the fracture of partial end portions of anchor shanks, the fracture of central portions of anchor ropes (shanks), repeated repair of supporting areas, twisting, damage and failure of steel frames and other accidents will occur in the roadway supporting process.

In order to overcome these problems, Professor Manchao HE puts forwards a design concept of a new constant-resistance and large deformation material under the enlightenment of the philosophical thought of conquering the unyielding with the yielding and tampering force with mercy, and researches and develops a new anchor shank—a new constant-resistance and large deformation material (e.g., a constant-resistance and large deformation anchor shank disclosed in the Chinese invention patent Publication No. CN101858225A). Moreover, a whole set of control concept and technical equipment system with slope reinforcement, slope slide and earthquake disaster monitoring and early warning, and underground engineering support is formed on the basis and provides a good exploration mode for solving the problem of large deformation in geotechnical engineering.

After the research and development of the constant-resistance and large deformation anchor shank (rope), it is found that a large deformation tensile testing system is required for better systematically testing and researching mechanical properties of the constant-resistance and large deformation anchor shank (rope). Moreover, the mechanical properties of the constant-resistance and large deformation anchor shank (rope) are compared with those of a common deformation anchor shank (rope) under same experimental conditions, so as to achieve static parameters of the anchor shanks (ropes) to be tested, including the constant-resistance and large deformation anchor rope, are obtained by experiments, and draw relevant experimental curves of force and displacement, force and deformation, force and time and the like; moreover, to provide better support for large deformation of soft rock, large deformation of bump (rock-burst), large deformation of outburst, large deformation of slope slide, large deformation of seismogenic faults and the like by calculation and relevant measurements.

SUMMARY

The objective of the present disclosure is to overcome the defects in the related technology and provide a large deformation tensile testing system capable of accurately and effectively testing a large deformation tensile of an anchor shank or an anchor rope.

The objective of the present disclosure is achieved, for example, by the following technical solutions.

According to an aspect of the present disclosure, there is provided a large deformation tensile testing system, for use in testing the large deformation tensile of an anchor shank or an anchor rope. The large deformation tensile testing system comprises: a main frame; a rear collet component arranged at a first position in a longitudinal direction of the main frame; a front collet component movably arranged at a second position in the longitudinal direction of the main frame; a telescoping apparatus arranged near one end of the main frame, connected to the front collet component and configured to stretch a sample clamped between the rear collet component and the front collet component according to the set control scheme; and a measurement and control apparatus including a sensor module, a control module, an analysis module and an output module, wherein the sensor module is connected to the telescoping apparatus, senses a real-time displacement of the telescoping apparatus and a real-time tensile of the telescoping apparatus to the sample, and forms and transmits real-time displacement data and real-time tensile data to the analysis module and the control module; the control module is configured to control a testing process to be performed under set testing conditions, according to the set control scheme and an input from the sensor module; and the analysis module is configured to analyze an input from the sensor module, and form and transmit a test result to the output module; and the output module is configured to output the test result.

The large deformation tensile testing system of the present disclosure has at least one of the following advantages: by adoption of the large deformation tensile testing system provided by the present disclosure, the parameters of statics of various anchor shanks and anchor ropes, including the constant-resistance and large deformation anchor shank, can be accurately and effectively obtained; relevant experimental curves of force and displacement, force and deformation, force and time and the like can be drawn accurately and effectively; the radial direction and the lengthwise direction can be researched by calculation and relevant measurements; and better support is provided for large deformation of soft rock, large deformation of bump (rock-burst), large deformation of outburst, large deformation of slope slide, large deformation of seismogenic faults and the like.

Therefore, the large deformation tensile testing system of the present disclosure can adopt different control schemes to test the mechanical properties of various anchor shanks (ropes) by various means, and has the advantages of energy saving, environmental protection and high safety.

DETAILED DESCRIPTION

Detailed description will be given below to the preferred embodiments presenting the characteristics and advantages of the present disclosure. It should be understood that various variations may be made to different embodiments of the present disclosure without departing from the scope of the present disclosure, and the description and the drawings therein are only for illustration in essence and not intended to limit the present disclosure.

Figure 1:
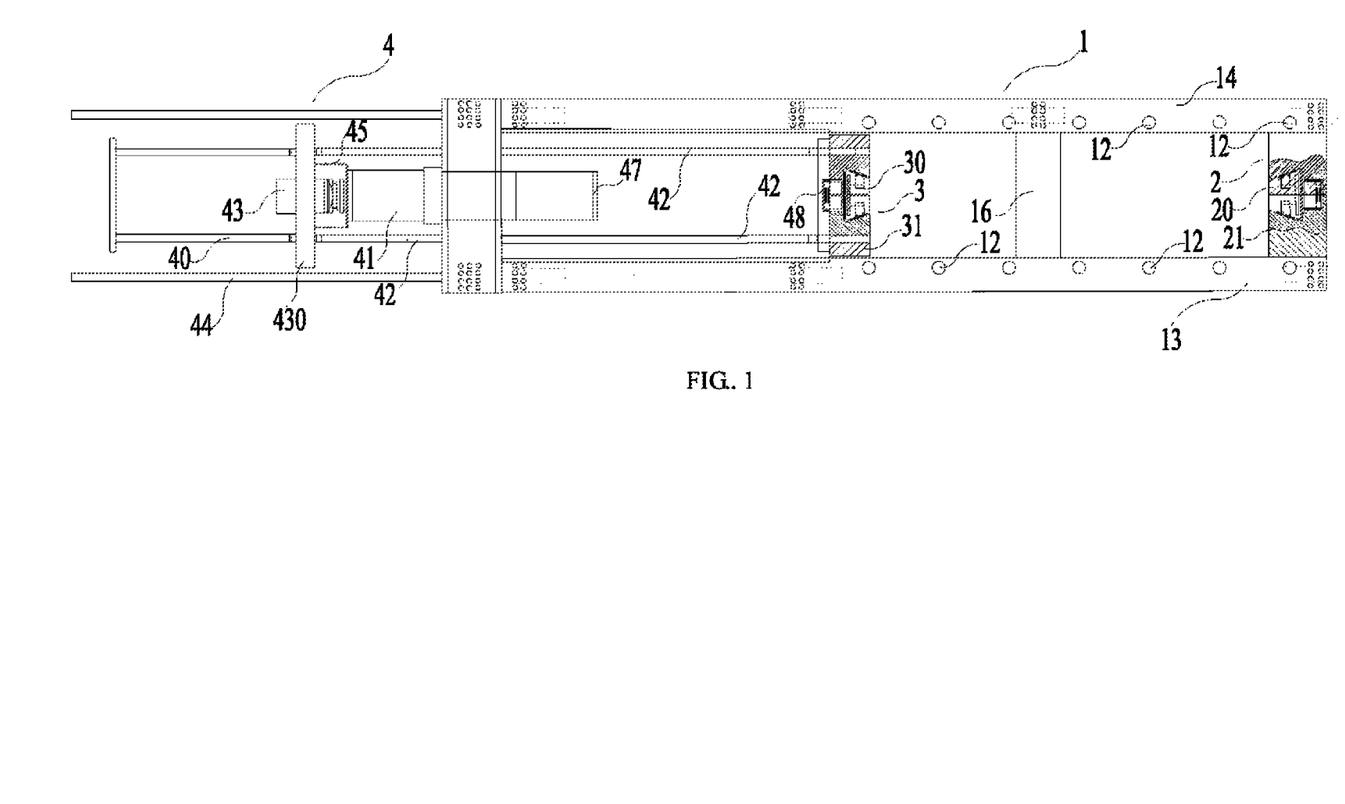
FIG. 1 is a schematic top view of a large deformation tensile testing system provided by an embodiment of the present disclosure.
Figure 2:
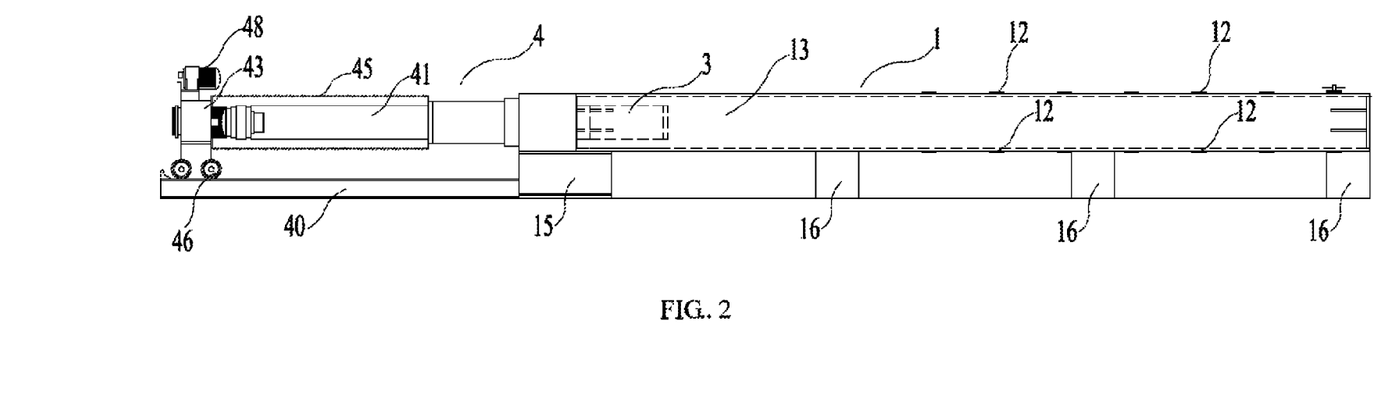
FIG. 2 is a schematic front view of the large deformation tensile testing system provided by the embodiment of the present disclosure.

As illustrated in FIGS. 1 and 2, the large deformation tensile testing system provided by an embodiment of the present disclosure may comprise five parts in view of function, namely a main frame 1, a front collet component 3, a rear collet component 2, a telescoping apparatus 4 and a measurement and control apparatus (not shown in the figure). The above five parts will be described below respectively.

1. Main Frame

The main frame 1 of the large deformation tensile testing system provided by an embodiment of the present disclosure adopts a horizontal frame structure. The main frame 1 is made of high-quality steel and hence has stable material performances, good compressive property and neat and elegant appearance.

The telescoping apparatus 4 is arranged at one end of the main frame 1. Therefore, for convenience of description, the one end of the main frame 1 provided with the telescoping apparatus 4 is taken as a front end, and the other end is taken as a rear end. The front and the rear of other components are also based on this.

As illustrated in FIGS. 1 and 2, the main frame 1 comprises two grooved longitudinal girders 13 and 14 being arranged in parallel and having U-shaped cross sections; the grooved longitudinal girders 13 and 14 have U-shaped openings which are opposite to each other; and the grooved longitudinal girders 13 and 14 are supported below by a front support 15 and a plurality of rear supports 16, wherein as the front support 15 upper supports a piston cylinder 41 in the telescoping apparatus 4, the longitudinal length of the front support 15 must be greater than that of the rear supports 16.

To ensure the safety of the test and avoid the damage due to sudden breakage of a sample and the like, a safety net crossing the grooved longitudinal girders 13 and 14 may be arranged to cover between upper surfaces of upper flanges of the grooved longitudinal girders 13 and 14. In order to facilitate the movement of the safety net, rails may be arranged on upper surfaces of the grooved longitudinal girders 13 and 14, and guide wheels may be arranged at bottom ends of the safety net, so that the safety net can be easily pushed on the rails.

2. Front Collet Component and Rear Collet Component

As illustrated in FIGS. 1 and 2, the front collet component 3 and the rear collet component 2 are arranged opposite to each other, and may have same shape (profile). In order to facilitate the movement of the front collet component 3 and the rear collet component 2, clamps 30 and 20 of the front collet component 3 and the rear collet component 2 are arranged on beams 31 and 21, respectively, and both ends of the beams 31 and 21 are supported on upper surfaces of lower flanges of the grooved longitudinal girders 13 and 14, respectively. Moreover, in order to facilitate the movement of the beams 31 and 21, guide wheels may be arranged on upper surfaces of lower flanges of the beams 31 and 21.

The difference is that the front collet component 3 must move in the testing process, but the rear collet component 2 is immovable in the testing process. As the front collet component 3 must be connected with the piston cylinder 41 before test, the front collet component 3 is immovable. As for the rear collet component 2, in order to clamp samples with different lengths, a plurality of through holes 12 for fixing the rear collet component 3 are formed on upper flanges and lower flanges of the grooved longitudinal girders 13 and 14. In the case of fixation, a screw rod matched with the diameter of the through holes 12 runs from top to bottom through the through holes 12 on the upper flanges of the grooved longitudinal girders 13 and 14, a through hole on the beam 21, and the through holes 12 on the lower flanges of the grooved longitudinal girders 13 and 14, and a fixed pin runs through the screw rod, so as to fix the rear collet component 2. The front collet component 3 may also be fixed in a way as same as the rear collet component 2.

Apart from the samples with different lengths, in order to improve the universality of the large deformation tensile testing system provided by an embodiment of the present disclosure, both the rear collet component 2 and the front collet component 3 may include a plurality of sets of clamps adapted to different samples, so as to be adapted to different diameters and shapes of the samples. The clamps may include V-shaped clamps, flat clamps, strand-specific clamps, anchor shank-specific sleeve clamps and the like, and the clamps may be used for the tensile test of various materials such as anchor shanks (ropes), strands, plates and bars. Therefore, the large deformation tensile testing system provided by the present disclosure is a versatile test equipment.

Moreover, the large deformation tensile testing system provided by the present disclosure may be also for use in testing the statics performances in the case of sample compression. In such case, a stay plate 48 is arranged on a front end surface of the beam 31, and a stay plate 47 is arranged on a rear end surface of the piston cylinder 41; a sample to be compressed is placed between the stay plates 47 and 48. If the piston cylinder 41 is started, the sample can be compressed.

The chuck assemblies 2 and 3 are both made of high-quality steel forgings; the built-in clamps 20 and 30 may be hydraulically actuated hydraulic clamps; and a manual button box may be adopted for control. Therefore, the samples can be easily clamped and the working efficiency can be improved.

3. Telescoping Apparatus

As illustrated in FIGS. 1 and 2, the telescoping apparatus 4 includes a connecting carriage 43, a pair of screw rods 42 and the piston cylinder 41. The screw rods 42 are fixedly connected between both sides of the beam 31 of the front collet component 3 and a connecting plate 430 of the connecting carriage 43; the two screw rods 42 are laterally symmetrical relative to the piston cylinder 41. A cylinder body of the piston cylinder 41 is fixedly connected to a front end of the main frame 1. A piston rod of the piston cylinder 41 is fixedly connected to the connecting plate 430 and extended towards a direction far away from the main frame 1. A gear reduction unit is arranged on the connecting carriage 43, and includes a beam motor 48. The gear reduction unit can automatically adjust the travel of the screw rods for facilitating the tensile test. As for the position adjustment of the rear collet component 2, as interval between the through holes 12 is fixed, the fine adjustment of the distance between the rear collet component 2 and the front collet component 3 cannot be achieved. But the gear reduction unit 48 can perform fine adjustment of the position of the beam 31, hence the fine adjustment of the travel of the screw rods can be performed so as to be adapted to more samples.

The telescoping apparatus 4 stretches, according to a set control scheme, a sample clamped between the rear collet component 2 and the front collet component 3 by transmission of the screw rods 42. The tensile of the piston cylinder 41 is controlled in a set control scheme relevant to a test project to be performed.

As illustrated in FIG. 1, rotary wheels 46 are arranged at bottom ends of the connecting carriage 43 and can roll on the rails 40 arranged in parallel to the longitudinal direction of the main frame 1.

In order to facilitate good operation of the piston rod of the piston cylinder 41 without being affected by the outside environment, a square housing 44 for covering the piston rod of the piston cylinder 41 may be arranged at a front end of the main frame 1. Meanwhile, a telescopic dustproof cover 45 may be also sleeved between the piston rod of the piston cylinder 41 and the connecting plate 430 of the connecting carriage 43, and can be elongated or shortened along with extending or shortening of the piston rod.

In the large deformation tensile testing system provided by an embodiment of the present disclosure, the piston cylinder 41 may be referred to as a main operating cylinder, and an auxiliary cylinder for providing power to clamp samples may be arranged between the front collet component 3 and the rear collet component 2. The piston cylinder 41, being a core component of the whole set of equipment, is made of forgings, and hence ensures a good quality. A piston in the piston cylinder 41 may adopt an internal static pressure bearing mechanism to have a function of making the piston in suspension. In addition, a hydraulic buffer may be arranged in the piston cylinder 41, so as to avoid the impact of the piston cylinder 41 in the case of sample breakage and hence avoid the damage of any component. Moreover, the telescoping apparatus 4 may also adopt force overrunning protection, overpressure protection, displacement overrunning protection, overcurrent and overvoltage protection, limit protection and the like to avoid man-made faults.

A hydraulic source of the piston cylinder 41 may be a servo-hydraulic source, and pumped hydraulic oil thereof enters a valve seat through an oil filter. The oil entered the valve seat is used for control of the test force of the main cylinder through a servo proportional valve. When a pressure of the oil reaches a pressure set by an overflow valve, excess oil overflows through the overflow valve and flows back to an oil tank. The pressure of the system can be observed at any moment through a pressure gauge. In order to ensure the reliability of the clamped sample, an independent auxiliary oil pump is adopted to control hydraulic chucks and does not interfere with the operation of the main operating cylinder.

The oil tank of the servo-hydraulic source comprises an enclosed oil tank to avoid secondary pollution, and the oil filter in the system may have a filtrating accuracy of 10 micrometers in order to filter impurities from the oil. After long-term use, the oil filter may be clogged due to too large amount of impurities. Therefore, a filter core should be replaced according to specific conditions, so as to ensure the cleanness of an oil piping system and improve the service life of hydraulic elements. Meanwhile, an air cooler is arranged and is automatically started to prevent the oil temperature from rising when the temperature exceeds the set value, and hence the hydraulic system can be always in the optimum working condition.

The servo proportional valve may be adopted for the closed-loop control of the telescoping apparatus 4, so as to perform the function of controlling the equal test force (equal displacement) loading, the test force (displacement) retaining, the equal test force (equal displacement) unloading of the piston cylinder 41 by changing the oil mass and the direction of the oil flowing across the high-frequency response servo proportional valve by means of changing voltage signals of a controller, thereby completing different test projects. Such function is performed by a true closed-loop control and not affected by the external environmental, hence ensures the accuracy of the test. Meanwhile, the high-frequency response servo proportional valve has a strong anti-pollution property, hence the system stability can be greatly improved.

The servo-hydraulic source may be equipped with a load sensitive system to ensure that the outlet pressure of a pump matches with the load pressure when a high-pressure system operates in low pressure; the difference of the outlet pressure and the load pressure is only the pressure difference of a throttle orifice, which is about 1 MPa; and excessive hydraulic oil flows back to the oil tank through the load sensitive throttle orifice when the outlet pressure is higher than the load pressure by 1 MPa. Therefore, the power loss in the case of high-pressure overflow can be reduced; the heat productivity of the system can be reduced; the noise of the system can be reduced; and the objective of energy saving can be achieved. Meanwhile, due to low heat productivity, the service life of the hydraulic elements can be improved; the leakage of the system can be reduced; and the system stability can be greatly improved.

In the large deformation tensile testing system provided by the present disclosure, the maximum test force of the telescoping apparatus 4 applied to the sample may be up to 500 kN; the test force is stepless (continuously) and infinitely variable; the travel of the piston cylinder 41 may be up to 1,200 mm; the travel of the screw rods (the screw rods 42) may be in a range between 0 to 1,000 mm; and the sample can be stretched by 0 to 1,100 mm.

4. Measurement and Control Apparatus

The measurement and control apparatus may be further subdivided into a sensor module, a control module, an analysis module and an output module.

The sensor module is connected to the telescoping apparatus 4, senses the real-time displacement of the piston rod in the telescoping apparatus 4 and the real-time tensile of the telescoping apparatus to the sample, thus forms real-time displacement data and real-time tensile data, and then transmits the data to the control module for control and transmit the data to the analysis module for analysis, so as to form a test result.

The control module may control the normal operation of the testing process. The control module may include a console, an electric control box and a handheld control box. Most parts of the control module may be arranged on the same console provided with buttons for controlling the test and a display screen for displaying the test result. A main power switch and the like may be arranged on a side surface of the console. The control box may be arranged on a table of the console, and a panel of the control box is provided with an emergency stop button for controlling the piston cylinder 41 to stop in emergency, a start/stop button for controlling the piston cylinder 41, a start/stop button for controlling the auxiliary oil pump, a temperature control meter and the like, so that the operation is very convenient. Moreover, a computer may also be arranged in the console, and a display of the computer is also arranged on the table of the console. The test control mode may be selected and analysis results, etc. may also be outputted via the display of the computer.

In the large deformation tensile testing system provided by the present disclosure, before starting of the test, a plurality of test control modes may be selected; and in the testing process, both control rates and control functions may be mutually switched. For instance, various control modes such as test force constant-velocity control (e.g., application of 5 KN test force each minute), displacement constant-velocity control (e.g., 1 mm displacement each minute), constant test force, constant deformation and constant displacement rate may be selected for the large deformation tensile test of the sample.

In the testing process, the control module controls the testing conditions in real time by receiving real-time data fed back by a displacement sensor, a load sensor such as a pressure sensor, and a deformation sensor, so as to satisfy the test requirements.

Additionally to the control of the testing process, the control module also has the function of controlling the hydraulic clamp 30. The clamp 30 may be controlled by a button switch on the handheld control box. The beams are controlled by buttons in a click control mode. The clamping and loosening of nipper jaws are controlled by self-locking buttons which are pressed in working state and released in stop state.

The electric control box performs master control of a circuit of the large deformation tensile testing system of the present disclosure, and may be independently placed between the main frame 1 and the console.

The analysis module is generally operated by an operating data analysis program of the computer in the console and configured to analyze data according to a common analysis method in the field and further obtain the test result which is hence outputted by the output module. The data may be acquired based on test requirements.

The output of the output module mainly comprises two aspects: one is the output of the test result, and the other is the output of intermediate test data. The test result may be outputted by the display, and the test data may be stored in the hardware of the computer. The test result may also be outputted by the externally connected display screen. The intermediate test data may also be outputted in real time by the display of the computer and the externally connected display screen.

As a result of the computer control, almost all the operations are performed on a virtual panel, and hence the operations can be viewed directly and convenient. Thus the setting of test parameters, the test control, and the data analysis and processing can be easily completed. The testing process, the force-time curve, the force-displacement curve, the force-deformation curve and the like can be displayed on the screen in real time; and the test reports and the curves are printed by a printer.

By means of the control module, not only automatic control over the testing process through the computer can be performed, but also manual control over the testing process through the computer can be performed.

Simple description will be given below to the specific operating procedures of the large deformation tensile testing system provided by the present disclosure:

1) starting the computer in the console;
2) starting a control part: checking an oil source, turning on the main power switch, and pressing the start button of the auxiliary oil pump;
3) mounting the clamps 30 and 20 (it is required to confirm that the auxiliary oil pump is in the static state), and clamping the sample, in which a clamping portion of the sample must exceed the position of a half of the length of the clamps 20 and 30;
4) pushing the safety net to a position right over the sample;
5) starting a corresponding control software in the control module to create a new test project, and input an option information of relevant test control mode;
6) performing test: in the testing process, the sample is clamped between the clamps 30 and 20; the position of the clamp 20 is immovable; the clamp 30 is driven by the piston cylinder 41 to move toward the left side in FIG. 1; the piston rod of the piston cylinder 41 is extended towards the left side and drives the connecting carriage 43 to move; the connecting carriage 43 drives the screw rod 42 to move towards the left side as well, so that the beam 31 is driven to move towards the left side, and hence a large deformation tensile is applied to the sample clamped between the clamps 20 and 30; the sensor module senses the real-time displacement of the piston rod of the piston cylinder 41 through a cable encoder; and a large deformation extensometer in the sensor module senses the deformation of the sample.

pressing a stop key on the console and saving the test data after test;
7) removing the sample and returning the piston cylinder 41;
8) turning off the power supply.

Figure 3:
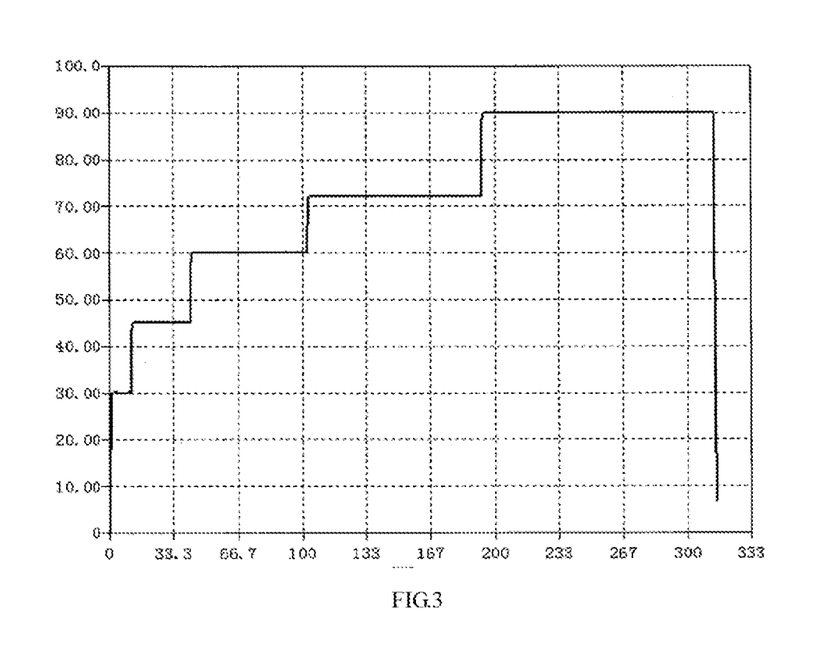
FIGS. 3 to 5 are test curve diagrams of a telescoping apparatus of the large deformation tensile testing system provided by the embodiment of the present disclosure.

By means of the large deformation tensile testing system of the present disclosure, various tests on anchor shanks (ropes) can be performed, such as the test of the fundamental performances of the anchor shanks, the creep test of temporary anchor shanks, the creep test of permanent anchor shanks, the relaxation test of anchor shanks, and the extension test of anchor shanks. The test result will be exemplarily illustrated as follows:

FIG. 3 shows a test curve diagram (force-time curve) in a creep test of a temporary anchor shank. In the test, an axial design value of 60 kN is inputted, and the total test time is 5.25 hours. In FIG. 3, the unit of force on a longitudinal axis is kN and the unit of time on a transverse axis is minute. The test curve indicates that the sample can maintain the statics performances thereof under the tensile of less than 90 kN, but under the tensile of 90 kN, after a certain period of time, a constant-resistance material on the sample is departed from the anchor shank and the testing process ends.

Figure 4:
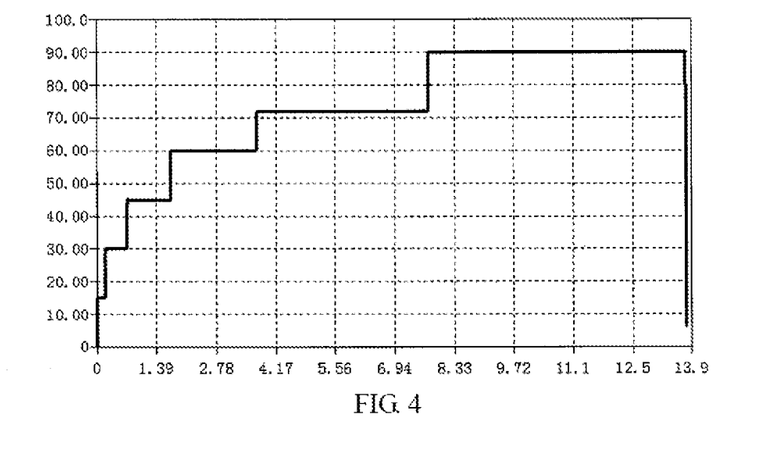

FIG. 4 shows a test curve diagram (force-time curve) in a creep test of a permanent anchor shank. In the test, an axial design value of 60 kN is inputted, and the total test time is 5.25 hours. As illustrated in FIG. 4, the unit of force on a longitudinal axis is kN and the unit of time on a transverse axis is hour. The test curve indicates that the sample can maintain the statics performances thereof under the tensile of less than 90 kN, but under the tensile of 90 kN, after a certain period of time, the constant-resistance material on the sample is departed from the anchor shank and the testing process ends.

Figure 5:
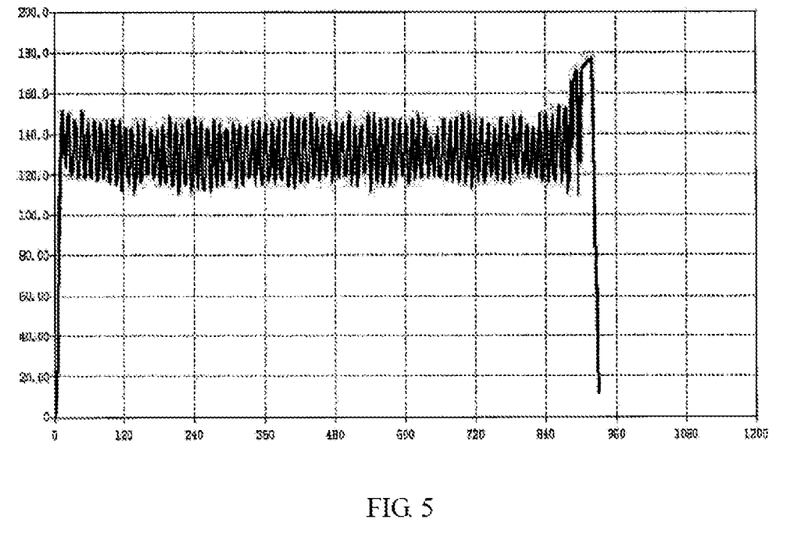

FIG. 5 shows a test curve diagram (force-displacement curve) in an extension test of an anchor shank. In the test, the control mode is the displacement control mode. In FIG. 5, the unit of force on a longitudinal axis is kN and the unit of displacement on a transverse axis is millimeter. The test curve indicates that the sample can maintain the statics performances thereof under the displacement of less than 900 mm, but when the displacement exceeds 900 mm, the constant-resistance material on the sample is departed from the anchor shank and the testing process ends.

The technical proposal has been disclosed above with reference to the preferred embodiments. It should be understood by those skilled in that variations and modifications made without departing from the scope and spirit of the present disclosure disclosed by the appended claims of the present disclosure all fall within the scope of protection of the appended claims of the present disclosure.

The invention claimed is:

1. A large deformation tensile testing system, for use in testing a large deformation tensile of an anchor shank or an anchor rope, wherein the large deformation tensile testing system comprises:
   a main frame;
   a rear collet component arranged at a first position in a longitudinal direction of the main frame;
   a front collet component movably arranged at a second position in the longitudinal direction of the main frame;
   a telescoping apparatus arranged near one end of the main frame, connected to the front collet component, and configured to stretch a sample clamped between the rear collet component and the front collet component according to a set control scheme; and
   a measurement and control apparatus including a sensor module, a control module, an analysis module, and an output module, wherein the sensor module is connected to the telescoping apparatus, senses a real-time displacement of the telescoping apparatus and a real-time tensile of the telescoping apparatus to the sample, forms real-time displacement data and real-time tensile data, and transmits the data to the analysis module and the control module; the control module is configured to control a testing process to be performed under set testing conditions, according to a set control scheme and an input from the sensor module; the analysis module is configured to analyze an input from the sensor module, and form and transmit a test result to the output module; and the output module outputs the test result,
   wherein the telescoping apparatus stretches the sample thought a piston cylinder; and clamps for clamping the sample between the front collet component and the rear collet component are hydraulic clamps, and
   wherein the main frame includes two grooved longitudinal girders being arranged in parallel and having U-shaped cross sections, wherein U-shaped openings of the two grooved longitudinal girders are opposite to each other; the telescoping apparatus includes a connecting carriage, a pair of screw rods, and the piston cylinder, wherein the pair of screw rods are connected between the front collet component and a connecting plate of the connecting carriage, a cylinder body of the piston cylinder is fixedly connected to one end of the main frame, and a piston rod of the piston cylinder is connected to the connecting plate and extended away from the main frame.

2. The large deformation tensile testing system according to claim 1, wherein the measurement and control apparatus further includes a console provided with control buttons and a display screen for displaying the test result.

3. The large deformation tensile testing system according to claim 1, wherein the sensor module includes a large deformation extensometer for measuring deformation and a guyed encoder for measuring the displacement of the piston cylinder.

4. The large deformation tensile testing system according to claim 1, wherein each of the rear collet component and the front collet component includes a plurality of sets of clamps for adapting different samples.

5. The large deformation tensile testing system according to claim 1, wherein a first stay plate is arranged at a rear end surface of the piston cylinder; a second stay plate is arranged at a front end surface of the front collet component; and the sample can be placed between the first stay plate and the second stay plate for compression test.

6. The large deformation tensile testing system according to claim 1, wherein each of an upper flange and a lower flange of the grooved longitudinal girder is evenly provided with a plurality of through holes for fixing the rear collet component.

7. The large deformation tensile testing system according to claim 6, wherein rotary wheels are arranged at bottom ends of the connecting carriage; and rails for rolling of the roller are arranged in parallel to the longitudinal direction of the main frame.

8. The large deformation tensile testing system according to claim 1, wherein a safety net is arranged to cover the main frame from above.

* * * * *